US012721855B2

(12) United States Patent
Liu et al.

(10) Patent No.: US 12,721,855 B2
(45) Date of Patent: Sep. 1, 2026

(54) ORAL Pt (IV) ANTICANCER PRODRUG CONTAINING 3-BROMOPYRUVATE AS AXIAL LIGAND

(71) Applicants: Yunnan Precious Metals Laboratory Co., Ltd, Kunming (CN); Kunming Medical University, Kunming (CN)

(72) Inventors: Weiping Liu, Kunming (CN); Chen Qing, Kunming (CN); Anli Gao, Kunming (CN); Peng Zhou, Kunming (CN); Jing Jiang, Kunming (CN); Hongyu Zhou, Kunming (CN); Juan Yu, Kunming (CN); Lingling Zhang, Kunming (CN)

(73) Assignees: Yunnan Precious Metals Laboratory Co., Ltd, Kunming (CN); Kunming Medical University, Kunming (CN)

( * ) Notice: Subject to any disclaimer, the term of this patent is extended or adjusted under 35 U.S.C. 154(b) by 388 days.

(21) Appl. No.: 18/508,200

(22) Filed: Nov. 13, 2023

(65) Prior Publication Data

US 2024/0100066 A1 Mar. 28, 2024

Related U.S. Application Data

(63) Continuation of application No. PCT/CN2023/074262, filed on Feb. 2, 2023.

(30) Foreign Application Priority Data

Feb. 18, 2022 (CN) ........................ 202210152055.9

(51) Int. Cl.

| | |
|---|---|
| ***A61K 31/555*** | (2006.01) |
| ***A61K 9/00*** | (2006.01) |
| ***A61P 35/00*** | (2006.01) |

(52) U.S. Cl.
CPC .......... *A61K 31/555* (2013.01); *A61K 9/0053* (2013.01); *A61P 35/00* (2018.01)

(58) Field of Classification Search
CPC .. A61K 31/555; A61K 9/0053; A61K 33/243; A61K 47/54; A61P 35/00; C07F 15/0093
See application file for complete search history.

(56) References Cited

FOREIGN PATENT DOCUMENTS

CN 113072594 A * 7/2021 .............. C07F 15/00

OTHER PUBLICATIONS

Ihrlund et al., Molecular Oncology 2008, 2, 94-101 (Year: 2008).*
Allen et al., Ansel's pharmaceutical dosage forms and drug delivery systems, 10th edition, Wolters Kluwer, 2014 (Year: 2014).*
CN113072594A_MT, Xin et al., Carbon glycoside glycosylated tetravalent platinum compound as well as synthesis method and application thereof, CN113072594A, Jul. 6, 2021, Machine Translation obtained from USPTO STIC machine translation services (Year: 2021).*

* cited by examiner

*Primary Examiner* — James H Alstrum-Acevedo
*Assistant Examiner* — Allen Chao

(57) ABSTRACT

Provided is an oral Pt(IV) anticancer prodrug containing a 3-bromopyruvate as an axial ligand, with a molecular formula of cis,trans,cis-[Pt(1R,2R-diaminocyclohexane)(OH)(3-bromopyruvate)($C_2O_4$)]. It is a prodrug of oxaliplatin and 3-bromopyruvic acid is a small molecular glycolysis inhibitor. The prodrug is able to simultaneously act on DNA replication and glycolytic pathways of cancer cells, giving full play to the advantage of double-acting targets. The oral Pt(IV) anticancer prodrug is synthesized by using oxaliplatin as a starting material, performing axial oxidation with $H_2O_2$ and neutralizing the oxidized product with 3-bromopyruvic acid.

2 Claims, 1 Drawing Sheet

Cisplatin Carboplatin Oxaliplatin

ORAL Pt (IV) ANTICANCER PRODRUG CONTAINING 3-BROMOPYRUVATE AS AXIAL LIGAND

CROSS-REFERENCE TO RELATED APPLICATIONS

The present application is a continuation application of PCT application No. PCT/CN2023/074262 filed on Feb. 2, 2023, which claims the benefit of Chinese Patent Application No. 202210152055.9 filed on Feb. 18, 2022. The contents of the aforementioned applications are incorporated by reference herein in their entirety.

TECHNICAL FIELD

The present disclosure relates to an oral Pt(IV) anticancer prodrug containing a 3-bromopyruvate as an axial ligand, with a molecular formula of cis,trans,cis-[Pt(1R,2R-diaminocyclohexane)(OH)(3-bromopyruvate)($C_2O_4$)]. It is a prodrug of oxaliplatin, and has a small molecular glycolysis inhibitor, 3-bromopyruvate, as a ligand in an axial direction. The complex of the present disclosure is able to simultaneously inhibit DNA replication and block glycolytic pathways of cancer cells, giving full play to the advantage of double-acting targets. It has good anti-cancer activity in vitro and vivo, especially higher inhibitory effect on tumor growth via oral administration and lower toxicity. The complex can be used for chemotherapy of malignant tumor, belonging to the field of biopharmaceuticals.

BACKGROUND

Malignant tumors, as the second leading cause of death worldwide just next to cardiovascular disease, are a major medical problem to be solved urgently. Surgery, radiotherapy and chemotherapy are three pillars of modern tumor treatment. Compared with surgery and radiotherapy characterized by local treatment, chemotherapy is systemic therapy based on cytotoxic drugs. It is not only the first choice for treatment of hematologic malignancies, but also is an important therapy for primary solid tumors and metastatic tumors. With the development of biomedicine, the consequent targeted therapy and immunotherapy have received much attention owing to their unique mechanisms of action and therapeutic effects. However, because of some disadvantages of a limited scope of benefit in clinical use, they cannot completely replace the conventional cytotoxic drugs. The cytotoxic drugs can directly kill cancer cells, rapidly dividing cells in particular, and inhibit tumor growth. They have the characteristics of a wide anti-cancer spectrum and high activity, being a cornerstone of chemotherapy. The cytotoxic drugs are also widely used in adjuvant therapy before or after surgery and radiotherapy, and play an extremely important role in the comprehensive treatment against cancers. Since chemotherapy can make up for the deficiency of targeted therapy and immunotherapy, it has become a tendency to combine chemotherapy with targeted therapy and immunotherapy in clinical treatment of cancer patients. Platinum anticancer drugs, represented by cisplatin (DDP) and carboplatin (CBP) and oxaliplatin (OXP) as shown in FIG. 1, are a kind of very important cytotoxic chemotherapeutic drugs. They have been listed in the pharmacopoeia of most countries and regions such as the United States, Japan, the European Union and China, and are widely used in the chemotherapy of clinical frequently-occurring malignant tumors. Platinum drugs target DNA of cancer cells at the molecular level and suppress DNA synthesis, therefore they have the advantages of high anticancer activity and great synergistic effect in combination with the targeted therapy and immunotherapy drugs. For example, the combined use of paclitaxel and cisplatin, the combined use of gefitinib and carboplatin, as well as the combined use of pembrolizumab and oxaliplatin all have achieved good clinical effects, and have become the first-line combination regimens. According to the latest statistics, of the combination chemotherapy regimens in current clinical use, above 50% contain the platinum anticancer drugs as one active ingredient.

However, the platinum anticancer drugs also have two major obstacles in clinical application, toxic side-effects and drug resistance. Platinum drugs belong to cytotoxic anticancer drugs and lack sufficient selectivity for cancer cells. While killing the cancer cells, they also damage normal cells to different degrees, often leading to myelosuppression, kidney injury, neurotoxicity, nausea and vomiting and other toxic side-effects. These toxic side-effects have become a key factor that limits the drug dosage during chemotherapy and affect the quality of life of patients. Congenital or acquired insensitivity and resistance of cancer cells to platinum drugs are important reasons for the failure of chemotherapy. Moreover, none of the platinum drugs currently approved for the market have oral activity and need to be administered by injection, which brings inconvenience for clinical medication, and also reduces the compliance of the patients with medication. Therefore, it still has important clinical value to develop a new platinum drug with excellent activity including oral activity and with low toxicity.

In recent years, scholars at home and abroad have developed a variety of new platinum candidate drugs, mainly Pt(IV) complexes, targeted Pt(II) complexes and nano drug delivery systems, by changing the valence state of platinum, introducing bioactive ligands or adopting new dosage forms. However, the development projects have not proceeded well and are facing many challenges.

The onset and progression of cancer is a complex process involving multiple factors and multiple pathways. Many studies have shown that increasing the acting targets of the platinum drugs may improve the therapeutic effect and reduce the drug resistance of cancer cells, which is an important strategy for developing new platinum drugs at present.

Normal cells typically use mitochondrial oxidative phosphorylation to metabolize glucose and switch over to glycolysis only when there is little or no oxygen, producing lactate as a byproduct. Cancer cells avidly consume glucose for energy by glycolysis to survive in the hypoxic environment of malignant lesions, a phenomenon known as the Warburg effect. This unique glucose metabolic pathway of cancer cells has identified the mitochondrion as a prime target for cancer therapy. In addition, cancer cells develop the ability to avoid apoptosis by various pathways that ignore the command to commit cellular suicide. Compounds that trigger apoptosis through selective action on mitochondrial target sites of cancer cells bypass defective upstream mechanisms and trigger apoptosis in tumor cells that are otherwise resistant.

3-bromopyruvic acid belongs to small molecular organic carboxylic acids, and is a hexokinase II inhibitor. It can target glycolysis of cancer cells and induce apoptosis of cancer cells, and thus has an anticancer effect. There are also studies indicating that 3-bromopyruvic acid can reverse the multidrug resistance of cancers and enhance the anti-cancer activity of other anticancer drugs including the platinum drugs. However, 3-bromopyruvic acid are very unstable chemically in water because of strong electron-withdrawing inductive effects of bromine. Although 3-bromopyruvic exhibits a certain anticancer activity in vitro, it is quickly degraded in vivo, and has no obvious anti-tumor effect. Therefore, stability has become one of the major obstacles to the anticancer effect of 3-bromopyruvic acid in vivo.

SUMMARY

The strategy used in the present disclosure is to introduce 3-bromopyruvic acid into the molecules of platinum drugs via coordinating bonds, so as to increase acting targets of the platinum drugs and improve the stability of 3-bromopyruvic acid.

Platinum drugs, already approved for clinical application such as cisplatin and carboplatin, and oxaliplatin, are Pt(II) complexes with a four-coordinate plane geometrical configuration, and have a general formula cis-[Pt(II)$A_2X_2$], where $A_2$ represents a carrier group which is $2NH_3$ or 1R,2R-diaminocyclohexane; and $X_2$ represents a leaving group which is $2Cl^-$, 1,1-cyclobutane dicarboxylate or $C_2O_4^{2-}$.

The Pt(II) complexes are a kind of kinetically active compounds for ligand substitution reactions. If the leaving group $X_2$ is not a strong ligand, Pt(II)-X coordination bond is weak and will quickly break down in an aqueous solution, forming active species cis-[Pt(II)$A_2(H_2O)_2]^{2+}$ which will readily react with other components throughout the body, thereby resulting in unpredictable toxicities. 3-bromopyruvic acid is a monocarboxylic acid with very weak coordinating ability, so that it may be inferred that a complex cis-[Pt(II)$A_2$(3-bromopyruvate)$_2$], formed by introducing 3-bromopyruvic acid into the molecules of Pt(II) drugs via coordination bonds, is poor in stability and may be degraded before arriving at a tumor site in the body.

Pt(IV) complexes, formed by Pt(II) drugs through axial oxidation, have a hexa-coordinate octahedron geometrical configuration. They are chemically stable and relatively inert to ligand substitution reactions. Numerous studies have demonstrated that in comparison with the Pt(II) complexes, the reaction rate of the Pt(IV) complexes with biological macromolecules is obviously reduced, so they can maintain stability in the in vivo environment, and the toxicity will be mitigated. Tumor cells are generally in a hypoxia state and in a reductive micro-environment where the concentration of glutathione and vitamin C is obviously higher than that in the normal cells. Glutathione and vitamin C are known to be important bio-reductive agents and can reduce Pt(IV) to Pt(II), releasing the axial ligands and forming a corresponding Pt(II) anticancer drug, as illustrated in the following reaction.

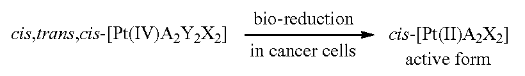

Therefore, the Pt(IV) complex may be regarded as a prodrug of Pt(II), so as to provide a better way for the tumor-targeted delivery of the Pt(II) drugs. Furthermore, through selecting a proper axial ligand, the Pt(IV) complex may be endowed with good water solubility and lipid solubility, so that the Pt(IV) complex is suitable for multiple administration routes, especially oral administration. Introducing other anti-cancer moiety with different action mode in an axial direction may also increase therapeutic targets, enhancing anti-tumor activity.

The technical solution of the present disclosure is to introduce 3-bromopyruvic acid into oxidized Pt(IV) species of cisplatin, carboplatin, and oxaliplatin in the axial direction, so as to form Pt(IV) complexes with the following chemical formulas:

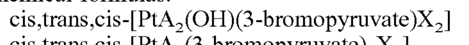
cis,trans,cis-[Pt$A_2$(OH)(3-bromopyruvate)$X_2$]

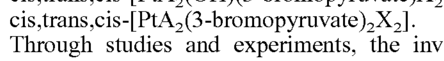
cis,trans,cis-[Pt$A_2$(3-bromopyruvate)$_2X_2$].

Through studies and experiments, the inventors have successfully synthesized two Pt(IV) complexes containing one 3-bromopyruvate in the axial direction, namely BrPt-2 and BrPt-3, and chemical formulas are:

BrPt-2

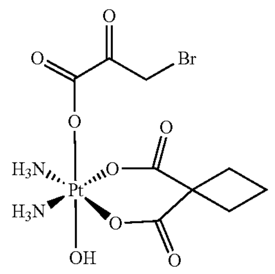

BrPt-3

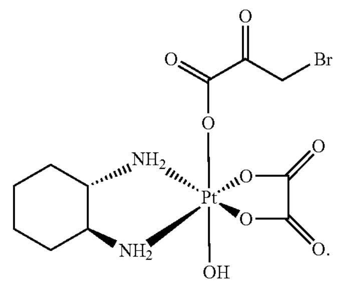

The inventors also found that when $X_2$ is $2Cl^-$, the corresponding Pt(IV) complexes, cis,trans,cis-[Pt$(NH_3)_2$(OH)(3-bromopyruvate)$Cl_2$] and cis,trans,cis-[Pt$A_2$(3-bromopyruvate)$_2C_2$] were very unstable in the aqueous solution, and would quickly degrade upon their formation, so they are unable to be prepared. In addition, in the aqueous solution system, even the amount of 3-bromopyruvic acid used in the synthetic process was increased to four times the calculated dosage, the product obtained after separation was still identified to be BrPt-2 or BrPt-3 which contains only one 3-bromopyruvate ligand, suggesting it is very difficult to prepare Pt(IV) complexes with two axial 3-bromopyruvate groups, as shown in the following chemical structure.

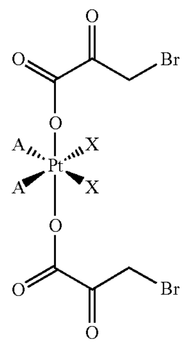

BrPt-2 is the prodrug of carboplatin while BrPt-3 is the prodrug of oxaliplatin. Their water solubility measured at room temperature is 4.3 mg/mL and 8.2 mg/mL, respectively. No obvious changes in $^{1}$H-NMR were monitored within 72 hours when BrPt-2 or BrPt-3 was dissolved in $D_2O$, indicating they are relatively stable in water. Therefore, the water solubility and stability of both BrPt-2 and BrPt-3 meet the requirements as platinum drug candidates.

BrPt-2 and BrPt-3, the Pt(IV) complexes involved in the present disclosure, can be synthesized by using carboplatin and oxaliplatin as a starting material, respectively. Oxidation with hydrogen peroxide converts Pt(II) drugs into Pt(IV) intermediates. The reaction of the Pt(IV) intermediates with excess 3-bromopyruvic acid in water will produce the desired compounds, BrPt-2 and BrPt-3.

The standard MTT method was adopted to measure the anticancer activity of platinum complexes against human cancer cells including non-small cell lung cancer cell line (A549), colon cancer cell line (HCT116) and liver cancer cell line (HepG2). The cytotoxicity of platinum complexes to normal liver cell line (L02) was also tested for the purpose of comparison. Results reveal that BrPt-3 exhibits great inhibitory effect on the growth of cancer cells and its anticancer activity is superior to that of the corresponding Pt(II) parent drug-oxaliplatin. More importantly, it still exhibits relatively high activity on A549/OXP, a human cancer cell line resistant to oxaliplatin. Fortunately, the cytotoxicity of BrPt-3 to L02 was found to be less than that of oxaliplatin, indicating the considerable selectivity of BrPt-3 for cancer cells.

BrPt-3 was submitted for in vivo antitumor test on mice transplanted with S180 sarcoma. As evidenced by the testing results, the tumor inhibitory rate of BrPt-3 is greater than that of oxaliplatin after intraperitoneal injection. From the changes in body weight, thymus and spleen indexes, blood routine, liver function and kidney function indexes, and degree of bone marrow hyperplasia of mice after administration, it can be seen that the overall toxicity of BrPt-3, especially the marrow toxicity, is lower than those of oxaliplatin. In addition, BrPt-3 also displays good antitumor activity by oral administration, and the toxicity of intragastric administration is obviously lower than that of intraperitoneal injection, so BrPt-3 is very promising as an oral platinum anticancer drug.

From the data published in the literature, it is clear that the anticancer activity of the Pt(IV) complexes is generally inferior to that of the corresponding Pt(II) drugs, probably due to the insufficient bio-reduction of Pt(IV) to Pt(II). The reason why BrPt-3 exhibits greater anticancer activity than oxaliplatin, we believe, is the additional anticancer effect from 3-bromopyruvic acid (3-BrPA). The probable anticancer mechanism of BrPt-3 involves double-acting targets (see FIG. 2). One is DNA replication of the cancer cells inhibited by oxaliplatin and the other is the glycolysis pathways blocked by 3-bromopyruvic acid, as a result the combined anticancer effect has been realized.

It is surprising that BrPt-2 is comparable to carboplatin in terms of both in vitro anticancer activity and in vivo antitumor activity, suggesting that the type and structure of the carrier group and the leaving group may affect the synergistic effect of 3-bromopyruvic acid and the Pt(II) drugs.

Based on the above testing results, BrPt-3, a Pt(IV) complex of the present disclosure, has satisfactory water solubility and high stability, great anticancer effect and low toxicity. It also displays excellent oral anti-tumor activity and can be used as a prodrug of oxaliplatin for the treatment of malignant tumor by an oral administration.

BrPt-3

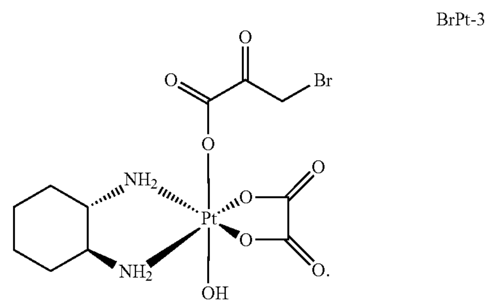

DETAILED DESCRIPTION

Example 1

Figure 1:
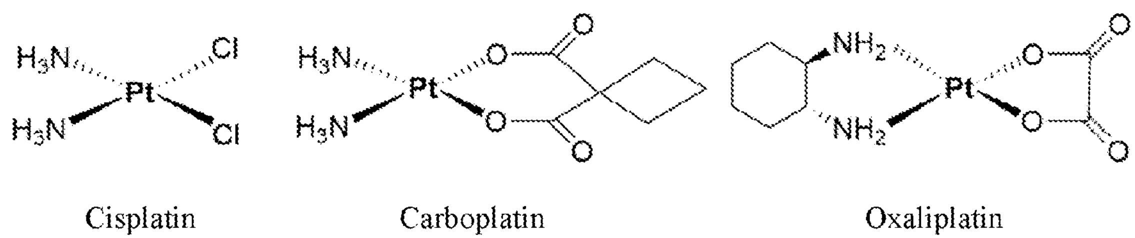
FIG. 1 is chemical structures of cisplatin, carboplatin, and oxaliplatin.
Figure 2:
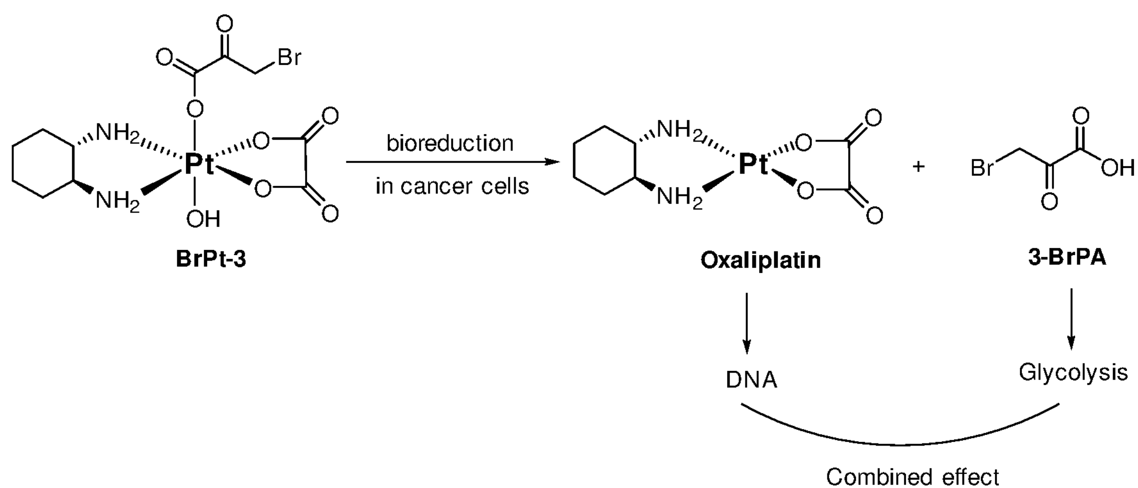
FIG. 2 is a schematic diagram of an anticancer mechanism of double-acting targets of BrPt-3 according to the present disclosure.

Synthesis of cis,trans,cis-[Pt(1R,2R-diaminocyclohexane)(OH)(3-bromopyruvate) ($C_2O_4$)] (BrPt-3)

6.0 g (15 mmol) of oxaliplatin, cis-[Pt(1R,2R-diaminocyclohexane)($C_2O_4$)], was dissolved in 600 mL of distilled water at 60° C. and 21.5 ml of 30 wt % $H_2O_2$ was slowly dropwise added. The mixture solution was stirred for 5 hours and a white product, cis,trans,cis-[Pt(1R,2R-diaminocyclohexane)$(OH)_2$($C_2O_4$)], precipitated out. After cooled to room temperature, the product was collected by filtration, washed with icy water and dried at 60° C. Finally, the product was recrystallized in water to obtain 5.73 g of pure cis, trans,cis-[Pt(1R,2R-diaminocyclohexane) $(OH)_2$ ($C_2O_4$)]. The overall yield was 88%.

cis,trans,cis-[Pt/1R,2R-diaminocyclohexane)$(OH)_2$ ($C_2O_4$)] (2.01 g, 4.73 mmol) was suspended in 25 mL of water and 5 mL of an aqueous solution of 3-bromopyruvic acid (0.86 g, 5.15 mmol) was added, and they were reacted at 35° C. for 48 hours under stirring. The mixture gradually became clear during the reaction, companied by the precipitation of a yellow product. The resulting solution was subjected to vacuum rotary at 45° C. to near dryness and the residue was filtered out, washed with acetone twice and with ethanol twice, freeze dried to obtain 2.15 g of a crude product. The crude product was dissolved in 200 ml water and filtered to remove a small amount of insoluble substance, and freeze-dried again to give the pure and white crystalline powder of BrPt-3 (2.07 g) with the yield of 76.7%.

Structural characteristic parameters of BrPt-3 sample: <1> elemental analysis: measured values Pt 33.3%, C 22.6%, H 2.87%, N 4.78% (calculated values Pt 33.6%, C 22.8%, H 2.93%, N 4.82%); <2> $^1$H NMR ($CDCl_3$, 500 MHz) ζ7.41 (d, J=55.9 Hz, 2H, $NH_2$), 7.26 (s, $CDCl_3$), 7.05 (s, 2H, $NH_2$), 3.89 (s, 2H, $CH_2$-3-BrPA), 2.07 (d, J=33.6 Hz, 2H, 2CH-cyclohexyl), 1.64 (s, 2H, $CH_2$-cyclohexyl), 1.54 (s, $H_2O$), 0.85 (d, J=29.3 Hz, 2H, $CH_2$-cyclohexyl), 0.10 (d, J=10.9 Hz, 2H, $CH_2$-cyclohexyl), −0.00 (s, TMS), −0.12 (s, 2H, $CH_2$-cyclohexyl); $^{13}$C NMR (DMSO-$d_6$, 126 MHz): ζ 180.49 (s, 1C, COO-3-BrPA), 175.92 (d, J=22.4 Hz, 1C, $C_2O_4$), 175.42 (d, J=11.0 Hz, 1C, $C_2O_4$), 99.51 (d, J=174.2 Hz, 1C, CO-3-BrPA), 55.38 (d, J=12.1 Hz, 1C, $CH_2$—Br), 39.54 (dp, J=42.2, 21.1 Hz, DMSO), 34.65 (d, J=43.5 Hz, 2C, 2CH-cyclohexyl), 27.67 (d, J=16.2 Hz, 2C, 2CH-cyclohexyl), 15.40 (d, J=5.7 Hz, 2C, 2Ch-cyclohexyl); <3> IR ($cm^{-1}$, Kbr): 3436(m), 3211(m), 1652(s), 1347(s), 1210(s), 1148(s), 548(w), 471(w); <4> ESI-MS m/z 580 $[M]^+$, 414 $[M\text{-}BrCH_2COCOO]^{30}$. These parameters conform well to the chemical structure of BrPt-3.

Example 2

Anticancer Activity and Cytotoxicity of BrPt-3, the Pt(IV) Complex of the Present Disclosure Oxaliplatin (OXP) was provided by Kunming Gui Yan Pharmaceutical Co. Ltd; and five human tumor cell lines (A549, A549/OXP, HCT116 and HepG2) and one human normal liver cells line (L02) were purchased from Cell Bank of Shanghai Institutes for Biological Sciences.

Effect of BrPt-3 and OXP on cell proliferation was detected by MTT assay. Cells at the logarithmic growth phase were seeded into 96-well plates, 90 μl/well, and incubated in a 5% $CO_2$ incubator for 24 h to allow cells to adhere.

The compound to be tested, BrPt-3 or OXP, was dissolved in 5% glucose solution (GS) just before MTT assay and 5 different concentrations were prepared. To a well, 10 μl of the compound was added and each concentration was provided with 4 parallel repeated wells. And then the cells were cultured in 5% $CO_2$ incubator for 48 h. After that, 20 μl of MTT (5 mg/ml) was added to each well and the plate was continued to be incubated for another 4 hours.

After the incubation, each well was added with 100 μl of DMSO to dissolve the reduced product formazan. An OD value was measured at 570 nm and 630 nm using a microplate reader, and the inhibitory rate was calculated and the concentration of 50% inhibition (ICso) was given using SPSS software.

TABLE 1

Effect of the tested compounds on proliferation of different tumor cell lines

| Tested compounds | Exposure time/h | $IC_{50}$ (μM, Mean ± SD, n = 4) | | | | |
|---|---|---|---|---|---|---|
| | | A549 | A549/OXP | HCT116 | HepG2 | L02 |
| OXP | 48 | 18.2 ± 0.80 | 211.0 ± 22.2 | 27.1 ± 1.40 | 29.7 ± 1.32 | 9.78 ± 0.60 |
| BrPt-3 | 48 | 17.2 ± 1.49 | 78.6 ± 12.7 | 14.0 ± 0.80 | 11.7 ± 2.63 | 13.4 ± 0.12 |

The results show that compared with OXP, BrPt-3 of the present invention has high inhibitory activity on the proliferation of human tumor cell lines A549, HCT116 and HepG2. The activity of BrPt-3 against oxaliplatin-tolerant lung cancer cell line A549/OXP was also higher than that of oxaliplatin, indicating that BrPt-3 can overcome the resistance of tumor cells to OXP to a certain extent. The results are listed in Table 1.

In addition, for normal hepatocyte line L02, $IC_{50}$ value of BrPt-3 was larger than that of oxaliplatin, indicating BrPt-3 is less toxic to normal cells and shows higher selectivity for tumor cells.

Example 3

Tumor Growth Inhibitory Effect and Preliminary Toxicity of BrPt3, the Pt(IV) Complex of the Present Disclosure Kunming (KM) mice, 22-25 g, female, were purchased from Hunan Slack Laboratory Animal Co., Ltd. Mouse sarcoma 180 (S180) strain was provided by Chinese Academy of Sciences Shanghai Institute of Materia Medica. Both BrPt-3 and OXP were prepared into required concentration with 5% GS just prior to the administration.

S180 cells grown well in mouse ascites were abstracted and adjusted to $10^7$/ml with NS, and were subcutaneously inoculated into the right armpit of mouse, 0.2 ml/mouse. After 24 hours of inoculation, mice were randomly divided into 3 groups: solvent control (5% GS), positive control (OXP) and BrPt-3 subjects, and administered intraperitoneally once a day for 13 consecutive days. Doses were selected with reference to our pre-experiments and the literature data. 24 hours after the last administration, the mice were fasted for 12 hours and then the tumor was taken out and weighed, and the tumor growth inhibitory rate was calculated. Data were represented as mean±standard deviation, and P values were analyzed using SPSS statistical software. In addition, the effect of the tested compounds on the body weight, vital organs and blood indicators of the mice was observed to assess the preliminary toxicity of BrPt-3.

1) Anti-Tumor Activity

Compared with the solvent control, OXP and BrPt-3 had obvious tumor growth inhibitory activity, and the inhibitory rate was 67.8% and 76.8%, respectively, but they displayed different degrees of adverse effect on the body weight of mice, with OXP being most obvious. Considering both the antitumor activity and body weight loss of the mice following the administration, it can be seen that the therapeutic effect of BrPt-3 is better than OXP. The results are shown in Table 2.

TABLE 2

Effect of the tested compounds on the growth of mouse transplanted tumor S180

| Groups | Dosage | Scheme of administration | Number of mice: Beginning of experiment | Number of mice: End of experiment | Body weight (g): Beginning of experiment | Body weight (g): End of experiment | Body weight (g): Difference of body weight | Tumor weight (g) | Tumor inhibitory rate (%) |
|---|---|---|---|---|---|---|---|---|---|
| 5% GS | 0.2 ml | ip once/d × 13 d | 6 | 6 | 23.2 ± 0.96 | 26.5 ± 1.08 | 3.28 ± 0.85 — | 1.83 ± 0.32 | / |
| OXP | 7.6 μM/kg | | 6 | 6 | 22.9 ± 1.49 | 22.5 ± 1.94** | 0.34 ± 1.17*** | 0.59 ± 0.25*** | 67.8 |
| BrPt-3 | 7.6 μM/kg | | 6 | 6 | 23.7 ± 1.51 | 24.0 ± 1.74* | 0.27 ± 0.36*** | 0.43 ± 0.21*** | 76.8 |

Compared with the solvent control: *P < 0.05; P < 0.01; and *P < 0.001.

2) Effect on Vital Organs, Blood and Bone Marrow Indicators (1) The thymus and spleen, important immune organs, are the most common toxic targets of cytotoxic anticancer drugs. Compared with the solvent control, the thymus and spleen weight of mice in the dosing group were significantly reduced, indicating that oxaliplatin and BrPt-3 had immunosuppressive effects. By comparison, the immunosuppressive effect of OXP was more severe. The results are shown in table 3.

TABLE 3

Effect of the tested compounds on the spleen and thymus of tumor-bearing mice

| Groups | Dosage | Scheme of administration | Body weight without tumor | Number of mice: Beginning of experiment | Number of mice: End of experiment | Organ (g): Thymus | Organ (g): Spleen | Thymus index (mg/10 g) | Spleen index (mg/10 g) |
|---|---|---|---|---|---|---|---|---|---|
| 5% GS | 0.2 ml | ip once/d × 13 d | 26.5 ± 1.08 | 6 | 6 | 0.12 ± 0.01 | 0.14 ± 0.04 | 44.8 ± 3.35 | 48.3 ± 6.60 |
| OXP | 7.6 μM/kg | | 22.5 ± 1.94 | 6 | 6 | 0.02 ± 0.01*** | 0.04 ± 0.01*** | 8.09 ± 3.24*** | 16.7 ± 3.19*** |
| BrPt-3 | 7.6 μM/kg | | 24.0 ± 1.74 | 6 | 6 | 0.04 ± 0.01*** | 0.05 ± 0.02** | 14.8 ± 4.62*** | 22.4 ± 7.73*** |

Compared with the solvent control: *P < 0.05; P < 0.01; and *P < 0.001.

(2) The liver and kidneys are important organs for drug metabolism and the main toxic sites of platinum drugs. Compared to the solvent group, OXP and BrPt-3 appeared to have little adverse effect on the liver and kidney weight of the treated mice. The results are shown in Table 4.

TABLE 4

Effect of the tested compounds on the liver and kidney of tumor-bearing mice

| Groups | Dosage | Scheme of administration | Body weight without tumor | Number of mice: Beginning of experiment | Number of mice: End of experiment | Organ (g): Liver | Organ (g): Kidney | Liver coefficient (mg/g) | Kidney coefficient (mg/g) |
|---|---|---|---|---|---|---|---|---|---|
| 5% GS | 0.2 ml | ip once/d × 13 d | 26.5 ± 1.08 | 6 | 6 | 1.47 ± 0.23 | 0.35 ± 0.05 | 53.0 ± 1.41 | 13.0 ± 1.13 |
| OXP | 7.6 μM/kg | | 22.5 ± 1.94 | 6 | 6 | 1.18 ± 0.13* | 0.29 ± 0.05 | 52.5 ± 3.43 | 13.1 ± 2.60 |
| BrPt-3 | 7.6 μM/kg | | 24.0 ± 1.74 | 6 | 6 | 1.31 ± 0.21 | 0.30 ± 0.05 | 54.2 ± 5.15 | 12.6 ± 1.32 |

Compared with the solvent control: *P < 0.05.

(3) The concentrations of glutamate-acetone aminotransferase ALT and glutamate oxaloacetate aminotransferase AST in the blood are important indicators for reflecting hepatocyte damage, whereas serum creatinine CREA and urea nitrogen BUN levels are two important indicators of kidney function.

As shown in Table 5, compared with the solvent group, OXP could increase serum AST level in S180-bearing mice, but had no significant effect on ALT as well as CREA and BUN levels. However, BrPt-3 did not significantly seem to have any effect on liver function or kidney function.

TABLE 5

Effect of the test compounds on the liver and kidney functions of tumor-bearing mice

| Groups | Dosage | Scheme of administration | Number of mice | ALT (U/L) | AST (U/L) | CREA (μM/L) | BUN (mM/L) |
|---|---|---|---|---|---|---|---|
| 5% GS | 0.2 ml | ip | 3 | 47.80 ± 4.67 | 308.13 ± 52.0 | 11.30 ± 0.47 | 7.77 ± 0.12 |
| OXP | 7.6 μM/kg | once/d × | 3 | 52.30 ± 4.64 | 563.00 ± 23.7** | 11.70 ± 0.94 | 5.37 ± 1.72 |
| BrPt-3 | 7.6 μM/kg | 13 d | 3 | 41.40 ± 9.72 | 328.00 ± 38.6 | 11.70 ± 1.25 | 5.50 ± 1.10 |

Compared with the solvent control: *P < 0.05; and **P < 0.01.

(4) Myelosuppression is the most common toxicity associated with platinum drugs, usually a dose-limiting toxicity in clinical use, and is a major factor for the death of mice in acute toxicity tests. Changes in peripheral blood cell composition reflect the effect of the tested compound on bone marrow proliferative function. The experimental results showed that oxaliplatin and BrPt-3 reduced the number of PLT, WBC and RBC in the peripheral blood of S180-bearing mice compared with the solvent control, but the effect of OXP was more significant. Further results of bone marrow sternal smear revealed that the myeloproliferation level of the OXP group was extremely low, and that of the BrPt3 group was also reduced, indicating that OXP has more severe bone marrow suppression than BrPt-3. The results are shown in Table 6.

TABLE 6

Effect of the test compounds on general peripheral blood indexes of S180-bearing mice

| Groups | Dosage | Scheme of administration | Number of mice | WBC ($10^9$/L) | PLT ($10^9$/L) | RBC ($10^{12}$/L) |
|---|---|---|---|---|---|---|
| 5% GS | 0.2 ml | ip | 3 | 7.43 ± 1.71 | 893.00 ± 55.7 | 10.80 ± 1.22 |
| OXP | 7.6 μM/kg | once/d × | 3 | 1.21 ± 0.40* | 20.10 ± 5.44*** | 3.55 ± 1.44** |
| BrPt-3 | 7.6 μM/kg | 13 d | 3 | 3.27 ± 0.71 | 274.00 ± 76.9** | 8.74 ± 1.07 |

Compared with the solvent control: *P < 0.05; P < 0.01; and *P < 0.001.

Example 4

Oral Anti-Tumor Effect and Preliminary Toxicity of BrPt-3 of the Present Disclosure Kunming (KM) mice, about 18 g, female, were from Hunan Slack Laboratory Animal Co., Ltd; mice sarcoma 180 (S180) strain was provided by Chinese Academy of Sciences Shanghai Institute of Materia Medica. Both BrPt-3 and OXP were prepared into required concentration with 5% GS.

S180 cells grown well in mouse ascites were abstracted and adjusted to $10^7$/ml with NS, and were subcutaneously inoculated into the right armpit of mouse, 0.2 ml/mouse. After 24 hours of inoculation, mice were randomly divided into 3 groups: solvent control (5% GS), positive control (OXP) and BrPt-3 (ip, control) and BrPt-3 (ig) subjects, and administered intraperitoneally once a day for 13 consecutive days. Doses were selected with reference to pre-experiments and literature reports. 24 hours after the last administration, the mice were fasted for 12 hours and then the tumor was taken out and weighed, and the tumor growth inhibitory rate was calculated. T Data are represented as mean±standard deviation, and P values are analyzed using SPSS statistical software. In addition, the effects of the tested compound on the body weight, vital organs and blood indicators of mice were observed to initially assess the toxicity.

1) In Vivo Anti-Tumor Activity

Compared with the solvent group, BrPt-3, whether through intraperitoneal injection (ip) or intragastric administration (ig), could obviously inhibit the growth of mice S180, and at the dosage of 7.6 μM/kg, the tumor growth inhibitory rate was 52.3% and 48.4%, respectively. The inhibitory rate after ig administration was slightly lower than that after ip administration, while OXP is known to have no oral anti-tumor activity. In terms of the changes in the body weight of the tumor-bearing mice, ip administration of BrPt-3 retarded the growth of mice, while ig administration almost had no influence, suggesting that for BrPt-3 the overall toxicity of ig administration was reduced, compared to ip administration. The results are shown in Table 7.

TABLE 7

Effect of intraperitoneal injection (ip) and intragastric administration (ig) of the tested compound on growth of mice transplanted tumor S180

| Groups | Dosage | Administration scheme | Number of mice: Beginning of experiment | Number of mice: End of experiment | Body weight (g): Beginning of experiment | Body weight (g): End of experiment | Body weight (g): Difference of body weight | Tumor weight (g) | Tumor inhibitory rate (%) |
|---|---|---|---|---|---|---|---|---|---|
| 5% GS | 0.2 ml ip | once/d × 13 d | 6 | 6 | 18.60 ± 0.77 | 25.70 ± 2.11 | 7.10 ± 2.20 | 2.76 ± 0.17 | / |
| BrPt-3 | 7.6 µM/kg ip | | 6 | 6 | 18.90 ± 0.29 | 21.90 ± 1.03** | 3.00 ± 0.97*** | 1.24 ± 0.30*** | 55.3 |
| BrPt-3 | 7.6 µM/kg ig | | 6 | 6 | 19.30 ± 0.44 | 28.10 ± 1.98 | 8.79 ± 1.77 | 1.43 ± 0.43*** | 48.4 |

Compared with the solvent control group: *$P < 0.05$; $P < 0.01$; and *$P < 0.001$.

2) Effect of Ip and Ig Administration of the Tested Compound on Important Organs and General Peripheral Blood Indexes of S180-Bearing Mice The experimental results showed that the effect of BrPt-3 by ig administration on important organs and blood indexes of S180-bearing mice was less than that by ip administration. The bone marrow biopsy also demonstrated that the mouse bone marrow hyperplasia after ip administration of BrPt-3 was at an active level and was at a more active level after ig administration, indicating that the oral toxicity of BrPt-3 was lower than the toxicity caused by ip administration. The results are shown in Table 8-11.

TABLE 8

Effect of ip and ig administration of tested compound on spleen and thymus weights of S180-bearing mice

| Groups | Dosage | Administration scheme | Body weight without tumor | Number of mice: Beginning of experiment | Number of mice: End of experiment | Organ (g): Thymus | Organ (g): Spleen | Thymus index (mg/10 g) | Spleen index (mg/10 g) |
|---|---|---|---|---|---|---|---|---|---|
| 5% GS | 0.2 ml · ip | once/d × 13 d | 25.7 ± 2.11 | 6 | 6 | 0.09 ± 0.03 | 0.13 ± 0.03 | 36.60 ± 10.5 | 50.60 ± 13.70 |
| BrPt-3 | 7.6 µM/kg ip | | 21.9 ± 1.03 | 6 | 6 | 0.03 ± 0.01** | 0.05 ± 0.01*** | 12.80 ± 2.51** | 21.40 ± 3.78** |
| BrPt-3 | 7.6 µM/kg ig | | 28.1 ± 1.98 | 6 | 6 | 0.12 ± 0.01 | 0.15 ± 0.06 | 43.30 ± 7.06 | 53.00 ± 21.50 |

Compared with the solvent control: *$P < 0.05$; $P < 0.01$; and *$P < 0.001$.

TABLE 9

Effect of ip and ig administration of tested compound on liver and kidney weights of S180-bearing mice

| Groups | Dosage | Administration scheme | Body weight without tumor | Number of mice: Beginning of experiment | Number of mice: End of experiment | Organ (g): Liver | Organ (g): Kidney | Liver coefficient (mg/g) | Kidney coefficient (mg/g) |
|---|---|---|---|---|---|---|---|---|---|
| 5% GS | 0.2 ml · ip | once/d × 13 d | 25.7 ± 2.11 | 6 | 6 | 1.89 ± 0.19 | 0.38 ± 0.02 | 74.00 ± 8.29 | 14.80 ± 1.65 |
| BrPt-3 | 7.6 µM/kg ip | | 21.9 ± 1.03 | 6 | 6 | 1.34 ± 0.16** | 0.33 ± 0.02** | 61.00 ± 5.19* | 15.00 ± 0.72 |
| BrPt-3 | 7.6 µM/kg ig | | 28.1 ± 1.98 | 6 | 6 | 1.67 ± 0.18 | 0.35 ± 0.03 | 60.00 ± 6.34* | 12.60 ± 1.13 |

Compared with the solvent control: *$P < 0.05$; and **$P < 0.01$.

TABLE 10

| Effect of ip and ig administration of the tested compound on the liver and kidney functions of S180-bearing mice | | | | | | | |
|---|---|---|---|---|---|---|---|
| Groups | Dosage | Administration scheme | Number of animals | ALT (U/L) | AST (U/L) | BUN (mmol/L) | CREA (μmol/L) |
| 5% GS | 0.2 ml ip | once/d × 13 d | 3 | 56.9 ± 3.65 | 551 ± 35.0 | 11.9 ± 1.02 | 7.33 ± 0.94 |
| BrPt-3 | 7.6 μM/kg ip | | 3 | 33.5 ± 0.83** | 422 ± 73.8 | 13.1 ± 0.54 | 7.00 ± 0.82 |
| BrPt-3 | 7.6 μM/kg ig | | 3 | 58.8 ± 7.25 | 754 ± 233 | 19.3 ± 4.30 | 11.3 ± 2.36 |

Compared with the solvent control: *$P < 0.05$; and **$P < 0.01$.

TABLE 11

| Effect of ip and ig administration of the test compound on general peripheral blood indexes of S180-bearing mice | | | | | | |
|---|---|---|---|---|---|---|
| Groups | Dosage | Administration scheme | Number of animals | WBC ($10^9$/L) | PLT ($10^9$/L) | RBC ($10^{12}$/L) |
| 5% GS | 0.2 ml ip | once/d × 13 d | 3 | 9.65 ± 2.05 | 1089 ± 117 | 8.16 ± 1.02 |
| BrPt-3 | 7.6 μmol/kg ip | | 3 | 5.28 ± 1.36 | 542 ± 243* | 4.74 ± 0.88* |
| BrPt-3 | 7.6 μmol/kg ig | | 3 | 4.99 ± 0.20 | 716 ± 137* | 9.30 ± 0.12 |

Compared with the solvent control group: *$P < 0.05$; and **$P < 0.01$.

What is claimed is:

1. An oral Pt(IV) anticancer prodrug containing 3-bromopyruvate, a small molecular glycolysis inhibitor, as an axial ligand, with a molecular formula of cis,trans,cis-[Pt (1R,2R-diaminocyclohexane)(OH)(3-bromopyruvate) $(C_2O_4)$], wherein the oral Pt(IV) anticancer prodrug has a chemical structure as follows:

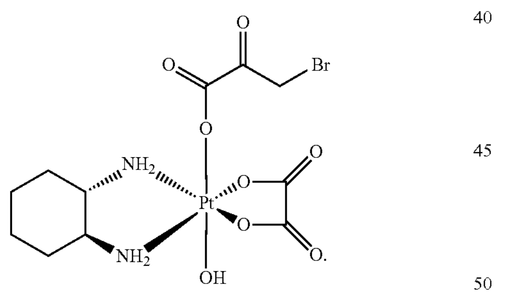

2. The oral Pt(IV) anticancer prodrug containing a 3-bromopyruvate axial ligand according to claim 1, wherein the oral Pt(IV) anticancer prodrug is formulated into an oral dosage form for treatment of colon cancer, lung cancer and liver cancer.

* * * * *